United States Patent
Sharps

(10) Patent No.: US 6,947,137 B2
(45) Date of Patent: Sep. 20, 2005

(54) SYSTEM AND METHOD FOR MEASURING BIREFRINGENCE IN AN OPTICAL MATERIAL

(75) Inventor: Robert W. Sharps, Corning, NY (US)

(73) Assignee: Corning Incorporated, Corning, NY (US)

( * ) Notice: Subject to any disclaimer, the term of this patent is extended or adjusted under 35 U.S.C. 154(b) by 89 days.

(21) Appl. No.: 10/733,792

(22) Filed: Dec. 11, 2003

(65) Prior Publication Data

US 2005/0128481 A1 Jun. 16, 2005

(51) Int. Cl.⁷ .............................. G01J 4/00; G02F 1/00
(52) U.S. Cl. ...................... 356/346; 356/365; 356/368; 356/369; 250/201.3; 359/322; 359/245
(58) Field of Search ................................ 356/364–370, 356/345, 451, 453, 455; 250/225, 234, 201.3; 359/322, 345, 369, 93

(56) References Cited

U.S. PATENT DOCUMENTS

| | | | | |
|---|---|---|---|---|
| 4,529,310 A | * | 7/1985 | Matsuda et al. | 356/457 |
| 4,914,487 A | * | 4/1990 | Croizer et al. | 356/35 |
| 5,243,455 A | * | 9/1993 | Johnson et al. | 349/18 |
| 5,504,581 A | * | 4/1996 | Nagata et al. | 356/364 |
| 5,521,705 A | | 5/1996 | Oldenbourg et al. | 356/368 |
| 5,949,480 A | * | 9/1999 | Gerhart et al. | 348/135 |
| 6,134,009 A | * | 10/2000 | Zavislan | 356/364 |
| 6,134,010 A | * | 10/2000 | Zavislan | 356/364 |
| 6,266,141 B1 | * | 7/2001 | Morita | 356/365 |
| 6,353,494 B1 | * | 3/2002 | Hamada | 359/322 |

OTHER PUBLICATIONS

R. Oldenbourg et al., "New polarized light microscope with precision universal compensator", Journal of Microscopy, vol. 180, Pt. 2, Nov. 1995, p. 140-147.
B. Wang et al., "A new instrument for measuring both the magnitude and angle of low level linear birefringence", Review of Scientific Instruments, vol. 70, No. 10, Oct. 1999, pp. 3847-3854.
R. Oldenbourg, "A new view on polarization microscopy", Nature, vol. 381, Jun. 27, 1996, pp. 811-812.

* cited by examiner

Primary Examiner—Gregory J. Toatley, Jr.
Assistant Examiner—Sang H. Nguyen
(74) Attorney, Agent, or Firm—William J. Tucker; Thomas R. Beall

(57) ABSTRACT

A system and method are described herein for determining the quality of an optical material by measuring and analyzing birefringence (e.g., stress-induced birefringence, inherent birefringence) in the optical material (e.g., glass sheet). The method is a scanning technique in which a birefringence sensor is set to a first optical state and then moved in a direction at a constant velocity over a glass sheet while first power transmission measurements are made at a high data rate. At the end of this move, the birefringence sensor is set to a second optical state and then moved at the same velocity back over the glass sheet, while second power transmission measurements are made. This procedure is repeated the same number of times as there are optical states in the birefringence sensor. A computer then calculates birefringence values using profiles of the power transmission measurements so as to determine the quality of the glass sheet.

20 Claims, 4 Drawing Sheets

SYSTEM AND METHOD FOR MEASURING BIREFRINGENCE IN AN OPTICAL MATERIAL

BACKGROUND OF THE INVENTION

1. Field of the Invention

The present invention relates to a system and method for determining the quality of an optical material by measuring and analyzing birefringence (e.g., stress-induced birefringence, inherent birefringence) in the optical material (e.g., glass sheet).

2. Description of Related Art

Birefringence is a characteristic of an anisotropic optical material where the index of refraction depends upon the direction of polarization of light that travels through the optical material. For example, polarized light that is oscillating up and down may be bent more when it passes through the optical material than polarized light that is oscillating from side to side. Birefringence can be inherent to the physical structure of the optical material (e.g., quartz crystals) or it can be induced in the optical material (e.g., glass sheet) by physical stress through the photoelastic effect. There are a number of well-known birefringence sensors that can be used to precisely measure the magnitude and orientation of birefringence in an optical material as described in the patent and articles listed below:

R. Oldenbourg et al. *"Polarized Light Microscopy"* U.S. Pat. No. 5,521,705, May 28, 1996.

R. Oldenbourg et al. *"New polarized light microscope with precision universal compensator"* J. Microscopy, V. 180, pp. 140–147, 1995.

B. Wang et al. *"A new instrument for measuring both the magnitude and angle of low level linear birefringence"* Rev. Sci. Instrum., V. 70, pp. 3847–3854, 1999.

The contents of these articles and the patent are hereby incorporated by reference herein.

Corning Inc. has developed a system that uses one of the well-known birefringence sensors to measure stress-induced birefringence along optical axes perpendicular to a plane of a Liquid Crystal Display (LCD) glass sheet. These stress-induced birefringence measurements are used to determine the stress levels internal to the glass sheet which are indicators of the quality of the glass sheet. To perform an accurate analysis of the stress levels in the glass sheet, multiple discrete birefringence measurements are required, either along the perimeter of the glass sheet or over the area of the glass sheet. And to obtain each discrete birefringence measurement, the system first moves a birefringence sensor to a data point on the glass sheet. The system then lets the birefringence sensor dwell at that data point while the sensor is cycled through multiple optical states and makes multiple power transmission measurements that enable a single birefringence value to be calculated at the data point. After determining the birefringence value at that data point, the system moves the birefringence sensor to the next data point on the glass sheet. The system then lets the birefringence sensor dwell while the sensor is cycled through multiple optical states and makes multiple power transmission measurements that enable a single birefringence value to be calculated at the data point. This process is repeated at each data point on the glass sheet.

The traditional system has a drawback in that it takes a relatively long time to perform the multiple power transmission measurements at one data point on the glass sheet which are needed to calculate a birefringence value. And, as can be appreciated the overall number of birefringence values measured and the total measurement time are at odds with one another since a large number of birefringence measurements provides for better spatial resolution while the total measurement time increases proportionally with the number of birefringence measurements. Another traditional system that has been used to increase the spatial resolution of birefringence measurements without incurring a time penalty includes the use of beam expanding optics to expand the optical measurement beam emitted from the birefringence sensor to illuminate a larger area on the glass sheet, and to use a pixilated detector such as a charge-coupled device (CCD) array. The sensitivity of this system is limited since the CCD array has a small dynamic range and the beam expanding optics introduce polarization impairments. Although the two systems mentioned above successfully enable one to determine the quality of an optical material by measuring and analyzing stress-induced birefringence in the glass sheet, it would be desirable to provide an alternative system that addresses the aforementioned shortcomings and other shortcomings of the traditional systems. This need and other needs are provided by the system and method of the present invention.

BRIEF DESCRIPTION OF THE INVENTION

The present invention includes a system and method that measures birefringence (e.g., stress-induced birefringence, inherent birefringence) in an optical material (e.g., glass sheet) in a manner that the sampling density of birefringence measurements can be increased while maintaining an enhanced spatial resolution without a substantial increase in measurement time. The method is a scanning technique in which a birefringence sensor is set to a first optical state and then moved in a direction at a constant velocity over a glass sheet while first power transmission measurements are made at a high data rate. At the end of this move, the birefringence sensor is set to a second optical state and then moved at the same velocity back over the glass sheet, while second power transmission measurements are made. This procedure is repeated the same number of times as there are optical states in the birefringence sensor. A computer then calculates birefringence values using profiles of the power transmission measurements so as to determine the quality of the glass sheet.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Referring to FIGS. 1–5, there are several diagrams associated with a system 100 and method 300 for measuring stress-induced birefringence in an optical material 110 (e.g., glass sheet 110) in accordance with the present invention. Although the system 100 and method 300 of the present invention are described herein where stress-induced birefringence is measured in the optical material 110, it should be understood that the present invention is not limited to measuring stress-induced birefringence but can be used to measure inherent birefringence or any type of birefringence regardless of its origin.

Figure 1:
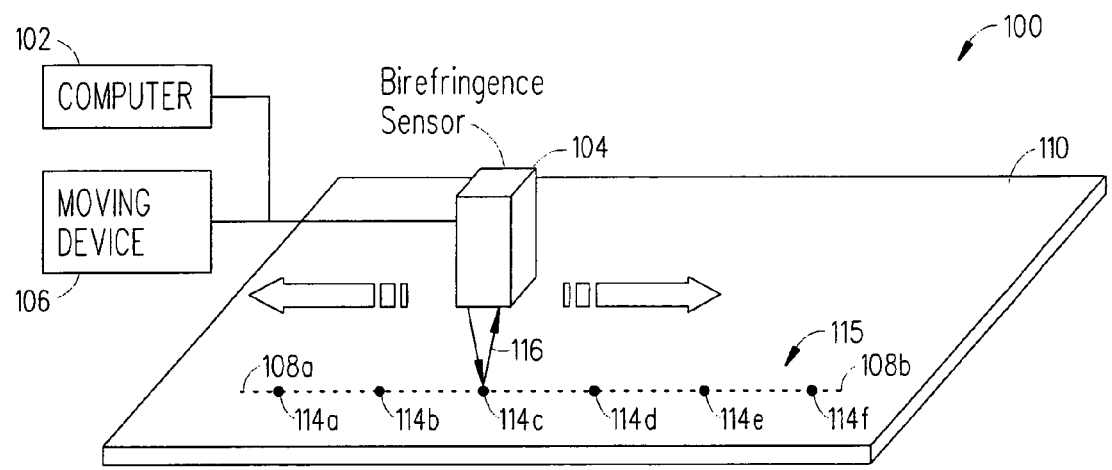
FIG. 1 is a block diagram illustrating a preferred system for measuring the stress-induced birefringence in a glass sheet in accordance the present invention.

As shown in FIG. 1, the system 100 includes a computer 102, a birefringence sensor 104 and a device 106 (e.g., stepper motor drive system 106, dc motor and ball screw drive 106). The device 106 moves the birefringence sensor 104 over the glass sheet 110. In operation, the birefringence sensor 104 is set (step 302 in FIG. 3) to a first optical state and then moved by the device 106 in a predetermined direction at a substantially constant velocity from a starting point 108a to an end point 108b over the glass sheet 110 while the birefringence sensor 104 emits and receives an optical measurement beam 116 and makes first power transmission measurements 112 along a path 115 including at distinct locations 114a, 114b . . . 114f on the glass sheet 110 (see FIGS. 1 and 2A). The first power measurements 112 are sent to the computer 102 and then the birefringence sensor 104 is set to a second optical state and moved by the device 106 in a predetermined direction at the same velocity as before from the end point 108b back to the starting point 108a over the glass sheet 110 while the birefringence sensor 104 emits and receives the optical measurement beam 116 and makes second power transmission measurements 118 along the path 115 including at distinct locations 114a, 114b . . . 114f on the glass sheet 110 (see FIGS. 1 and 2A). The second power measurements 118 are sent to the computer 102 and then this process is repeated (step 304 in FIG. 3) for as many times as there are optical states associated with the birefringence sensor 104. In this example, there are four optical states such that there are two more power transmission measurements 120 and 122 made along path 115 including at the distinct locations 114a, 114b . . . 114f on the glass sheet 110 (see FIGS. 1 and 2A). Then once this process (steps 302 and 304 in FIG. 3) is completed, the computer 102 calculates (step 306 in FIG. 3) birefringence values 124a, 124b . . . 124f (see FIG. 2B) along the path 115 or at distinct locations 114a, 114b . . . 114f on the glass sheet 110 using a combination of the power transmission measurements 112, 118, 120 and 122 (see FIG. 2A). Lastly, the computer 102 analyzes (step 308 in FIG. 3) the birefringence values 124a, 124b . . . 124f (see FIG. 2B) to determine the quality of the glass sheet 110. It should be appreciated that the two graphs shown in FIGS. 2A and 2B do not illustrate real data instead they are provided to help describe the operation of system 100 and scanning method 300.

The scanning method 300 described above and shown in FIG. 3 is a marked improvement over the traditional point-to-point scanning method. As described above, in the traditional scanning method for one birefringence value to be calculated at one position, the birefringence sensor must make multiple power transmission measurements at that position where one power transmission measurement is made at each of the optical states in the birefringence sensor. The birefringence sensor is then moved to a new position, and another set of power transmission measurements at different optical states are performed at the new position to enable the calculation of a birefringence value at that position. This process is repeated at each position or data point on the glass sheet. As a result, the traditional scanning method has a birefringence sampling that is quite coarse. In contrast, the scanning approach in method 300 differs in that the first power transmission measurements 112 are made at different positions 114a, 114b. 114f on the glass sheet 110 as the birefringence sensor 104 which is set at one optical state is moved along path 115 over the glass sheet 110. In this way, the method 300 generates a profile of the first power transmission measurements 112 as a function of the position 114a, 114b. 114f on the glass sheet 110 at a much finer interval. The birefringence sensor 104 is then set to a second optical state so it can make the second power transmission measurements 118. And, then the birefringence sensor 104 is moved back along the path 115 over the glass sheet 110 while generating a profile of the second power transmission measurements 118 as a function of the position 114a, 114b . . . 114f on the glass sheet 110. This process is repeated n-times depending on the number of optical states associated with the birefringence sensor 104. In this way, $n^{th}$ power profiles are recorded at very fine sampling intervals. Since $n^{th}$ power transmission measurements 112, 118, 120, 122 . . . readings exist for any position 114a, 114b, 114c, 114d, 114e, 114f . . . on path 115, a birefringence value 124a, 124b, 124c, 124d, 124e, 124f . . . can be calculated for any of those positions 114a, 114b, 114c, 114d, 114e, 114f. . . As such, one advantage of the scanning technique of method 300 is that it has a much finer birefringence sampling interval that can be made in a shorter period of time when compared to the traditional point-to-point scanning method. Other advantages associated with the scanning technique of method 300 when compared to the traditional point-to-point scanning method include (for example):

Greatly improved spatial resolution with a small amount of additional time investment.

Increased stability in the performance of the birefringence sensor 104 since the number of optical path adjustment cycles is greatly reduced.

The power transmission measurements can be obtained at a high data rate.

Reduced measurement costs since measurement throughput is much improved.

Figure 4:
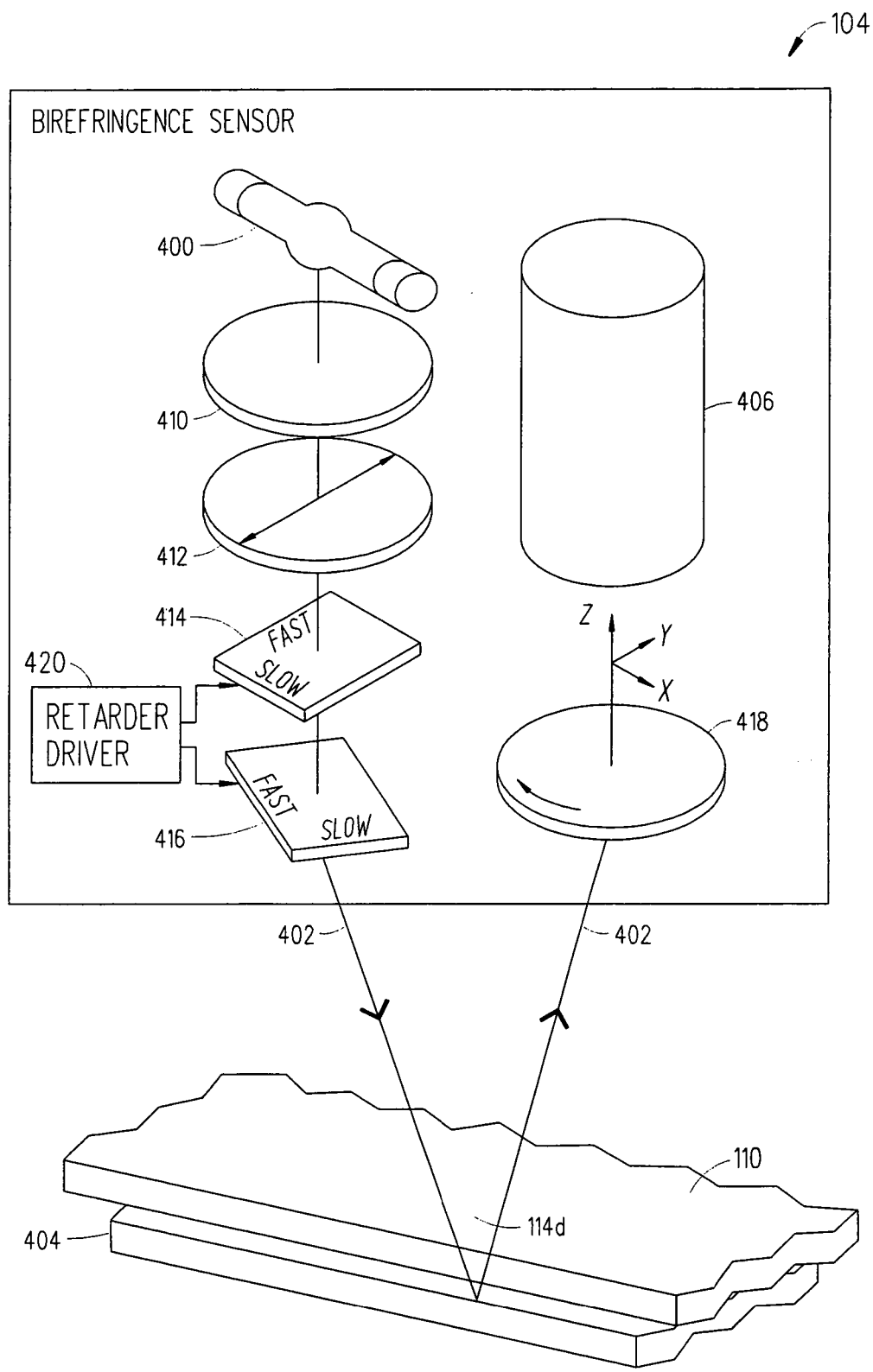
FIG. 4 is a diagram showing in greater detail the components of a liquid crystal variable retarder birefringence sensor that can be used in the system shown in FIG. 1.

Referring to FIG. 4, there is a diagram showing in greater detail the components of a liquid crystal variable retarder birefringence sensor 104 that can be used in system 100. The birefringence sensor 104 includes a mercury lamp 400 that emits an optical measurement beam 402 which illuminates the glass sheet 110 and then reflects off a mirror 404 positioned behind/under the glass sheet 110 and then passes back through the glass sheet 110 and into a general purpose light power meter 406 (detector 406). The light path between the mercury arc lamp 400 and the detector 406 also includes, on the illumination side, an interference filter 410 (provides monochromatic light), a linear polarizer 412 (mounted with its axis at 0° to a reference axis), and a pair of variable, liquid crystal, electro-optical retarders 414 and 416 with their principal slow axes positioned, respectively, at 45° and 0° to the reference axis. In the optical path on the imaging side of the glass sheet 110 and between the glass sheet 110 and the detector 406, is a right circular analyzer 418. In this embodiment, the variable retarders/electro-optic modulators 414 and 416 are liquid crystal devices. In other embodiments, other variable retarders/electro-optic modulators, such as Pockels cells, may be used. Similarly, another light source, e.g., incandescent lamp or laser, may be used in place of the mercury lamp 400. And, a monochrometer or the like may be used in lieu of the interference filter 410. The use of a lens located just above the glass sheet 110 is optional.

The birefringence sensor 104 functions when light 402 produced by the mercury arc lamp 400 is first filtered, and a narrow wave band (e.g., 546 mm) is selected and passed as polarized light by filter 410 and linear polarizer 412. Liquid crystal variable retarders 414 and 416 are set to different optical states by changing the voltage applied to each by the retarder driver 420. For example, in one optical state the retarder 414 acts as a quarter wave ($\lambda/4$) plate and retarder 416 acts as a half wave ($\lambda/2$) plate. When set as a quarter wave plate, variable retarder 414 causes the linearly polarized light 402 passed through it to become left circularly polarized. When set as a half wave plate, variable retarder 416 causes the left circularly polarized light 402 passed through it to become right circularly polarized. The right circularly polarized light 402 from retarder 416 illuminates a distinct location 114d (for example) on the glass sheet 110 and the light traversing any region of the glass sheet 110 is rendered elliptically polarized by any linear birefringence or dichroism in the region traversed on the glass sheet 110. Upon reflection from the mirror 404, the elliptically polarized light 402 changes hand from right to left. As the light 402 passes back through the glass sheet 110 additional polarization rotation is encountered. Thus, the image received by the right circular analyzer 418 contains elliptically polarized light 402. The amount of light 402 from each distinct location 114a, 114b . . . 114f on the glass sheet 110 that passes through the right circular analyzer 418, and the intensity of the light 402 that falls on the detector 406, depends on the extent of ellipticity of the light 402. The images (e.g., first power transmission measurements 112) produced by the light 402 incident on the detector 406 are recorded at a relatively fast sampling rate. The signals from the detector 406 are digitized and converted into integer values representing the intensities/power transmission measurements 122 (for example). This information is sent to the computer 102. And, then before the birefringence sensor 104 is moved again over the glass plate 110, the voltages applied to retarders 414 and 416 are changed by the retarder driver 420 to cause a change in the optical state or ellipticity of the light 402 incident on each of the distinct locations 114a, 114b . . . 114f of the glass sheet 110 and in the intensity of the light 402 incident on the detector 406. The total number of different movements the birefringence sensor 104 makes back and forth over the glass sheet 110 depends on the number of optical states the retarders 414 and 416 need to be changed in order to obtain enough power transmission measurements 112, 118, 120 and 122 to enable the computer 102 to determine the birefringence values 124a, 124b . . . 124f at corresponding locations 114a, 114b . . . 114f on the glass sheet 110. More details about some of the components and operation of this particular birefringence sensor 104 can be found by reading about another birefringence sensor in R. Oldenbourg et al. *"New polarized light microscope with precision universal compensator"* J. Microscopy, V. 180, pp. 140–147, 1995 and in U.S. Pat. No. 5,521,705. The contents of this article and patent are incorporated by reference herein. It should be appreciated that birefringence sensor 104 as used in this application has an enhanced performance when compared to traditional birefringence sensors like the one in the article by R. Oldenbourg.

Figure 2A:
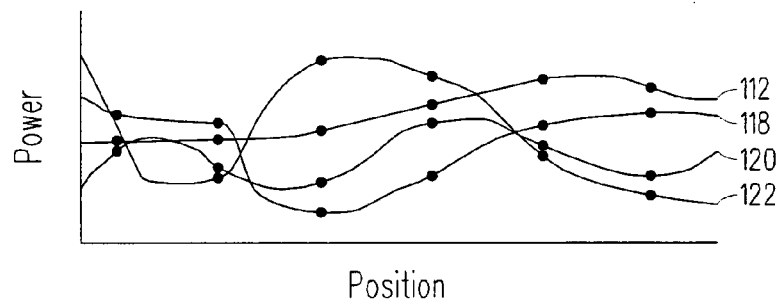
FIG. 2A is a graph that illustrates exemplary power transmission measurements relative to positions on the glass sheet measured by a birefringence sensor in the system shown in FIG. 1.
Figure 2B:
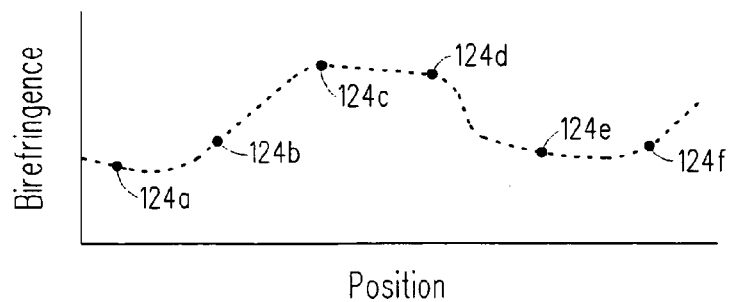
FIG. 2B is a graph that illustrates exemplary birefringence values relative to positions on the glass sheet that are obtained by analyzing the profiles of the power transmission measurements shown in FIG. 2A.
Figure 3:
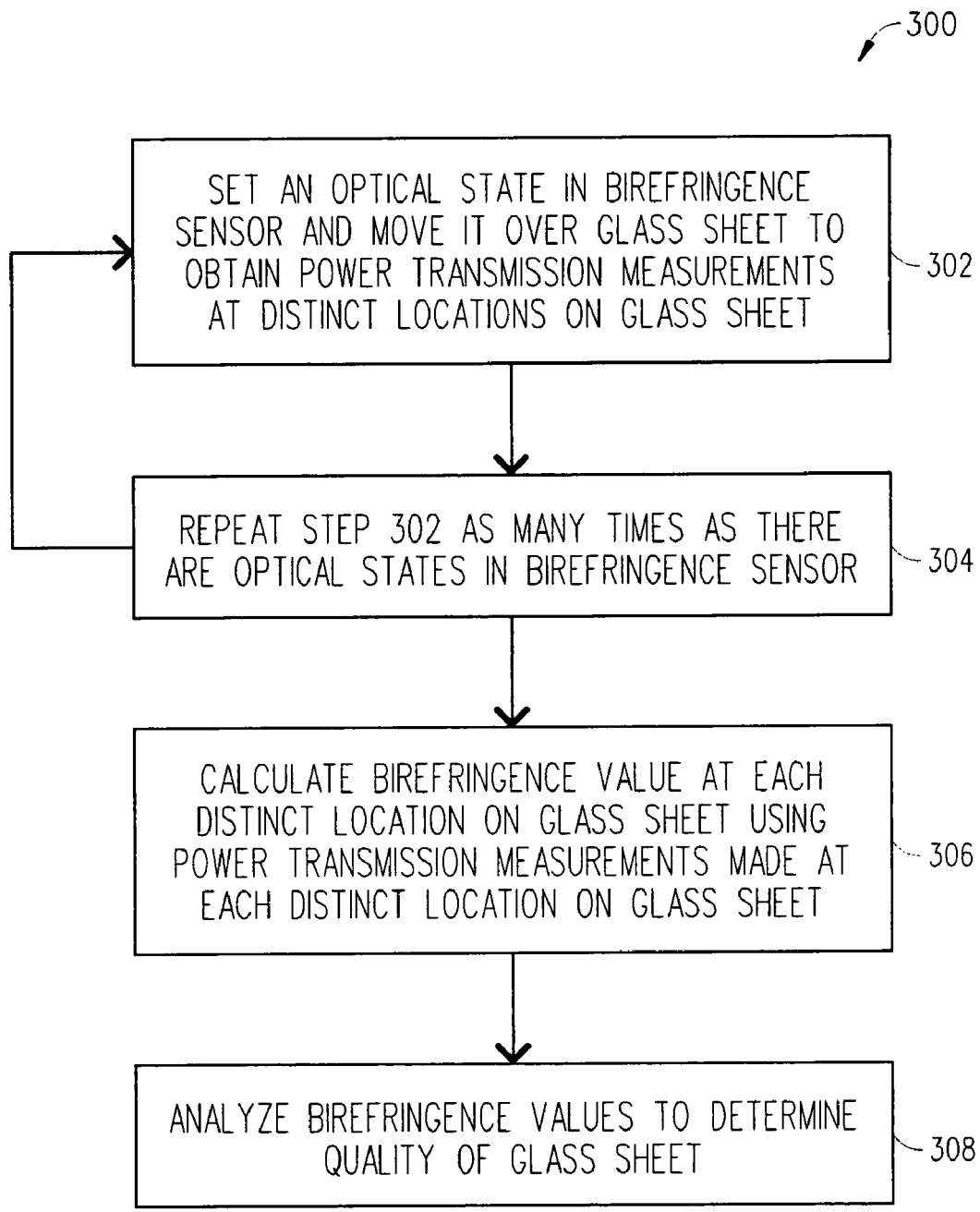
FIG. 3 is a flowchart illustrating the basic steps in a preferred method for measuring the stress-induced birefringence in a glass sheet in accordance with the present invention.
Figure 5:
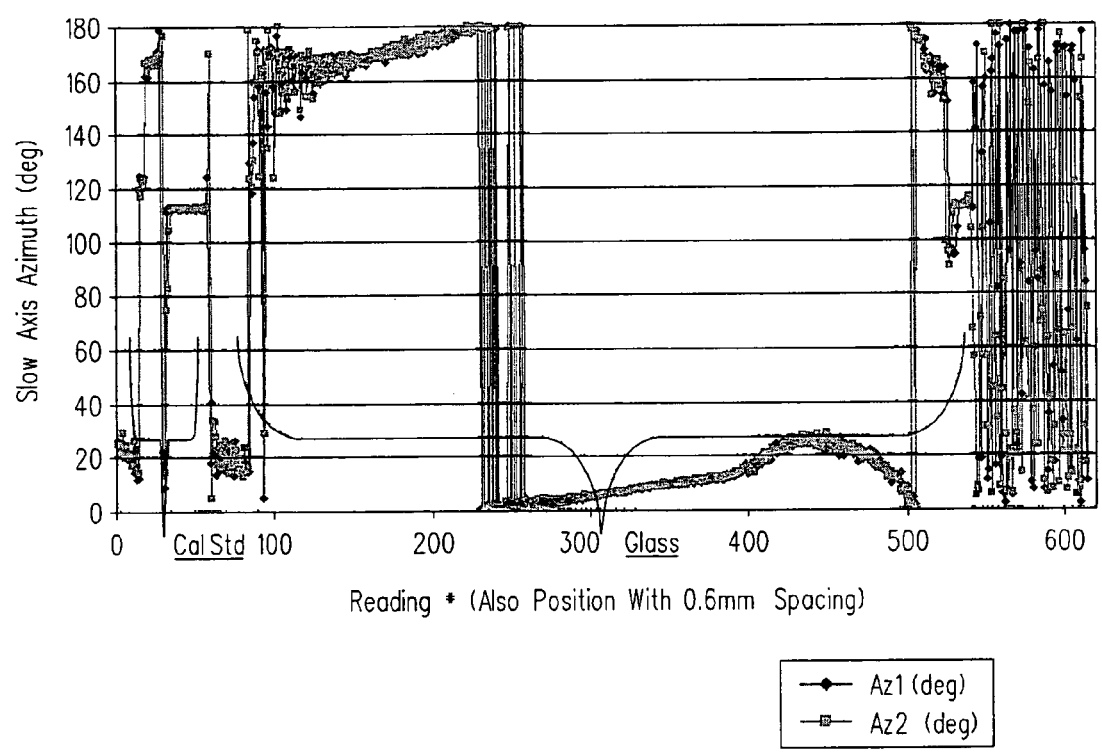
FIG. 5 is a graph that illustrates actual power transmission measurements relative to positions on the glass sheet that were measured by the system and liquid crystal variable retarder birefringence sensor shown in FIGS. 1 and 4.

Referring to FIG. 5, there is a graph that illustrates actual power transmission measurements vs. positions on the glass sheet 110 that were measured by the system 100 and the liquid crystal variable retarder birefringence sensor 104 shown in FIGS. 1 and 4 (compare to FIG. 2A). The retardance scans shown in this graph where made during the automatic motion of the birefringence sensor 104 on a 370 mm path length that included a 25 mm calibration slide and a 275 mm glass sheet 110.

Following are some advantages and uses of the system 100 and method 300 of the present invention:

The present invention includes a new scanning technique in which the number of birefringence measurement data points can be greatly increased without a substantial increase in the total measurement time.

One advantage the new scanning technique of the present invention has over the traditional discrete scanning technique is that it greatly increases the spatial resolution for glass stress measurement without incurring a substantial time penalty. For example, for a birefringence sensor that is moved at a velocity of 50 mm/sec and has a power transmission reading data rate of 50 Hz, a 1 mm sampling interval can be achieved for a 2000 mm profile length on a glass sheet in an estimated 160 seconds. For the same profile with the traditional discrete scanning technique using the same type of birefringence sensor would take an estimated 8000 seconds. One reason for this improvement is that in the traditional discrete scanning technique as the liquid crystal variable retarder birefringence sensor makes a single measurement, a pair of variable retarders is set to four different optical states and light transmission through the glass sheet 110 is recorded for each optical state. Whenever each of these retarders are set, additional time is required to allow for LC adjustment and settling before a stable power transmission measurement can be made. These adjustment and settling times are common to each discrete measurement point, and they contribute substantially to the overall sample measurement time in the traditional discrete scanning technique.

The birefringence sensor used in the present invention does not need to reflect the light off the mirror that is located behind/under the glass sheet as shown in FIGS. 1 and 4. Instead, the birefringence sensor can be configured so that light is transmitted just once through the glass sheet. In this case, the birefringence sensor would have multiple, components located on both sides of the glass sheet.

The birefringence sensor used in the present invention transmits an unexpanded optical beam to the optical material which enables the scanning approach to avoid the addition of performance impairing optics in the beam path and also enables the use of a high performance detector.

The scanning technique of the present invention can use any birefringence sensor in which any one birefringence measurement involves multiple readings at different launch and/or detect optical states. One example is the sensor described in detail by R. Oldenbourg et al. *"New polarized light microscope with precision universal compensator"* J. Microscopy, V. 180, pp. 140–147, 1995 and in U.S. Pat. No. 5,521,705. Another example of one such birefringence sensor is the photoelastic modulator (PEM) birefringence sensor that is described in detail in the article by B. Wang et al. *"A new instrument for measuring both the magnitude and angle of low level linear birefringence"* Rev. Sci. Instrum., V. 70, pp. 3847–3854, 1999.

The LCD glass sheets 110 described above can be made in accordance with a fusion process which is the preferred technique for producing sheets of glass used in LCDs because the fusion process produces sheets whose surfaces have superior flatness and smoothness compared to sheets produced by other methods. The fusion process is described in U.S. Pat. Nos. 3,338,696 and 3,682,609, the contents of which are incorporated herein by reference.

Although one embodiment of the present invention has been illustrated in the accompanying Drawings and described in the foregoing Detailed Description, it should be understood that the invention is not limited to the embodiment disclosed, but is capable of numerous rearrangements, modifications and substitutions without departing from the spirit of the invention as set forth and defined by the following claims.

What is claimed is:

1. A method for measuring birefringence in an optical material, said method comprising the steps of:
    setting a birefringence sensor to an optical state and moving said birefringence sensor in a predetermined direction at a substantially constant velocity over said optical material while making a power transmission measurement at each of a plurality of distinct locations on said optical material;
    repeating the setting step a predetermined number of times where each time said birefringence sensor is set to one of a predetermined number of optical states and moved in the predetermined direction at the substantially constant velocity over said optical material while making a power transmission measurement at each of the plurality of distinct locations on said optical material; and
    calculating a birefringence value for each distinct location on said optical material using a combination of the power transmission measurements measured at each distinct location on said optical material.

2. The method of claim 1, further comprising the step of analyzing said birefringence values to determine the quality of said optical material.

3. The method of claim 1, wherein said optical material is a glass sheet.

4. The method of claim 1, wherein said birefringence sensor is a liquid crystal variable retarder birefringence sensor.

5. A system comprising:
    a computer;
    a birefringence sensor;
    a device for moving said birefringence sensor over said optical material; and
    said birefringence sensor is set to a first optical state and then moved by said device in a predetermined direction at a substantially constant velocity from a starting point to an end point over said optical material while said birefringence sensor makes a first power transmission measurement at each of a plurality of distinct locations on said optical material which are sent to said computer then said birefringence sensor is set to a second optical state and moved by said device in a predetermined direction at the substantially constant velocity from the end point to the starting point over said optical material while said birefringence sensor makes a second power transmission measurement at each of the plurality of distinct locations on said optical material which are sent to said computer and this process is repeated a number of times depending on a number of optical states associated with said birefringence sensor then once the process is complete said computer calculates birefringence values for each distinct location on said optical material using a combination of the power transmission measurements measured at each distinct location on said optical material.

6. The system of claim 5, wherein said computer analyzes said birefringence values to determine the quality of said optical material.

7. The system of claim 5, wherein said optical material is a glass sheet.

8. The system of claim 5, wherein said birefringence sensor is a liquid crystal variable retarder birefringence sensor.

9. The system of claim 5, wherein said device is a stepper motor drive system.

10. The system of claim 5, wherein said device is a dc motor and ball screw drive.

11. A method for measuring birefringence in an optical material, said method comprising the steps of:
    setting a birefringence sensor to a first state and moving said birefringence sensor in a predetermined direction at a substantially constant velocity from a starting point to an end point over said optical material while making a first power transmission measurement at a plurality of distinct locations on said optical material;
    setting a birefringence sensor to a second state and moving said birefringence sensor in a predetermined direction at the substantially constant velocity from the end point to the starting point over said optical material while making a second power transmission measurement at the plurality of distinct locations on said optical material;
    setting a birefringence sensor to a third state and moving said birefringence sensor in the predetermined direction at the substantially constant velocity from the starting point to the end point over said optical material while making a third power transmission measurement at a plurality of distinct locations on said optical material;
    setting a birefringence sensor to a fourth state and moving said birefringence sensor in the predetermined direction at the substantially constant velocity from the end point to the starting point over said optical material while making a fourth power transmission measurement at the plurality of distinct locations on said optical material; and
    calculating a birefringence value at each distinct location on said optical material using the first, second, third and fourth power transmission measurements measured at each distinct location on said optical material.

12. The method of claim 11, further comprising the step of analyzing said birefringence values to determine the quality of said optical material.

13. The method of claim 11, wherein said optical material is a glass sheet.

14. The method of claim 11, wherein said birefringence sensor is a liquid crystal variable retarder birefringence sensor.

15. A system for measuring birefringence in an optical material, said system comprising:
- a computer;
- a birefringence sensor;
- a device for moving said birefringence sensor over said optical material;
- said birefringence sensor is set to a first optical state and moved by said device in a predetermined direction at a substantially constant velocity from a starting point to an end point over said optical material while said computer obtains from said birefringence sensor a first power transmission measurement at each of a plurality of distinct locations on said optical material;
- said birefringence sensor is set to a second optical state and moved by said device in a predetermined direction at the substantially constant velocity from the end point to the starting point over said optical material while said computer obtains from said birefringence sensor a second power transmission measurement at each of the plurality of distinct locations on said optical material;
- said birefringence sensor is set to a third optical state and moved by said device in the predetermined direction at the substantially constant velocity from the starting point to the end point over said optical material while said computer obtains from said birefringence sensor a third power transmission measurement at each of the plurality of distinct locations on said optical material;
- said birefringence sensor is set to a fourth optical state and moved by said device in the predetermined direction at the substantially constant velocity from the end point to the starting point over said optical material while said computer obtains from said birefringence sensor a fourth power transmission measurement at each of the plurality of distinct locations on said optical material; and
- said computer calculates birefringence values at each distinct location on said optical material using a combination of the first, second, third and fourth power transmission measurements measured at each distinct location on said optical material.

16. The system of claim 15, wherein said computer analyzes said birefringence values to determine the quality of said optical material.

17. The system of claim 15, wherein said optical material is a glass sheet.

18. The system of claim 15, wherein said birefringence sensor is a liquid crystal variable retarder birefringence sensor.

19. The system of claim 15, wherein said device is a stepper motor drive system.

20. The system of claim 15, wherein said device is a dc motor and ball screw drive.

* * * * *